United States Patent [19]

Conrow

[11] Patent Number: 5,457,245
[45] Date of Patent: Oct. 10, 1995

[54] PROCESS FOR PREPARATION OF CALCITRIOL LACTONE AND RELATED INTERMEDIATES

[75] Inventor: Raymond E. Conrow, Fort Worth, Tex.

[73] Assignee: Alcon Laboratories, Inc., Fort Worth, Tex.

[21] Appl. No.: 273,387

[22] Filed: Jul. 11, 1994

Related U.S. Application Data

[62] Division of Ser. No. 69,271, May 28, 1993, Pat. No. 5,354,872.

[51] Int. Cl.[6] .................................................. C07C 35/22
[52] U.S. Cl. .................................... 568/819; 549/313
[58] Field of Search .................................. 568/819

[56] References Cited

U.S. PATENT DOCUMENTS

| | | | |
|---|---|---|---|
| 4,594,432 | 6/1986 | Baggiolini et al. | 549/214 |
| 4,617,297 | 10/1986 | Boris et al. | 514/167 |
| 5,093,519 | 3/1992 | Bonillon et al. | 560/194 |
| 5,232,836 | 8/1993 | Bonillon et al. | 560/194 |

FOREIGN PATENT DOCUMENTS

| | | |
|---|---|---|
| 0454463 A2 | 10/1991 | European Pat. Off. . |
| 0532135A1 | 3/1993 | European Pat. Off. . |
| 4233051A1 | 4/1994 | Germany . |

OTHER PUBLICATIONS

Wovkulich et al., J. Org. Chem., vol. 48, p. 4433 (1983).
Yamamoto et al., J. Org. Chem., vol. 57, p. 33 (1992).
Gao et al., J. Am. Chem. Soc. vol. 109, 5765–5780 (1987).
Hatakeyama et al., J. Chem. Soc., Chem. Commun., p. 1229 (1992).
Johnson et al., J. Org. Chem., vol. 50, p. 2598 (1985).
Conron, R CA 120: 107454.

Primary Examiner—C. Warren Ivy
Assistant Examiner—Amelia Owens
Attorney, Agent, or Firm—Patrick M. Ryan

[57] ABSTRACT

A process for synthesizing (23S,25R)-calcitriol lactone and related Vitamin D analogs comprises reacting protected enantiomerically pure glycidol or 2-alkylglycidol with protected De-A,B-8β-hydroxy-24-nor-cholan-23-al, removing the protective groups from the epimeric product mixture and separating the epimers, to give a hydrindane tetrol product, followed by oxidation and protection of the hydrindane tetrol product, reacting the tetrol product with the lithium salt of (3S)-(3α,5β,Z)-2-(2-methylene-3,5-bis-((1,1-dimethylethyl)dimethylsilyloxy)cyclohexylidene)ethyl diphenyl phosphine oxide and removing the final protective groups. Certain intermediate compounds also show biological activity as angiostatic agents.

17 Claims, No Drawings

PROCESS FOR PREPARATION OF CALCITRIOL LACTONE AND RELATED INTERMEDIATES

This is a continuation of U.S. patent application Ser. No. 08/069,271 filed May 28, 1993, now U.S. Pat. No. 5,354,872.

This invention is directed to a process for synthesizing (23S,25R)-calcitriol lactone (1a), a biologically active metabolite of Vitamin D. The process is also useful for the synthesis of the (23R,25R), (23R,25S) and (23S,25S) diastereoisomers (respectively 1b, 1c and 1d) of 1a, as well as certain homologs of these compounds. Certain of the intermediate compounds also show biological activity as angiostatic agents and therefore are useful in therapy of anglogenesis-related disorders.

calcium absorption and utilization.

Only very small amounts of Compound 1a are obtainable from natural sources. Practical supply of 1a must therefore rely on chemical synthesis. Several synthetic sequences leading to 1a have been reported (See Hatakeyama et al., *J. Chem. Soc., Chem. Commun.*, 1229 (1992); and Yamamoto et al., *J. Org. Chem.* Vol. 57, p. 33), (1992). In each case, a critical issue is the construction of the lactone portion comprising carbons 23 through 27, with the stereochemistry at carbons 23 and 25 established in a controlled manner.

Of the several known sequences leading to Compound 1a, the most efficient has been reported by Johnson and Chan (Johnson et al., *J. Org. Chem.*, Vol. 50, p. 2598, (1985), the entire contents of which are hereby incorporated by reference in the present specification). Johnson et al. teach a synthesis of hydrindane triol 2a ($R^2$=$CH_2Ph$) in eight chemical steps from aldehyde 5 ($R^2$=$CH_2Ph$). These workers furthermore describe the debenzylation of 2a ($R^2$=$CH_2Ph$) to tetrol 3a, and oxidation of 3a to keto lactone 4a. The conversion of 4a to 1a is known (Wovkulich et al., *J. Org. Chem.*, Vol. 48, p. 4433, (1983), the entire contents of which are hereby incorporated by reference in the present specification).

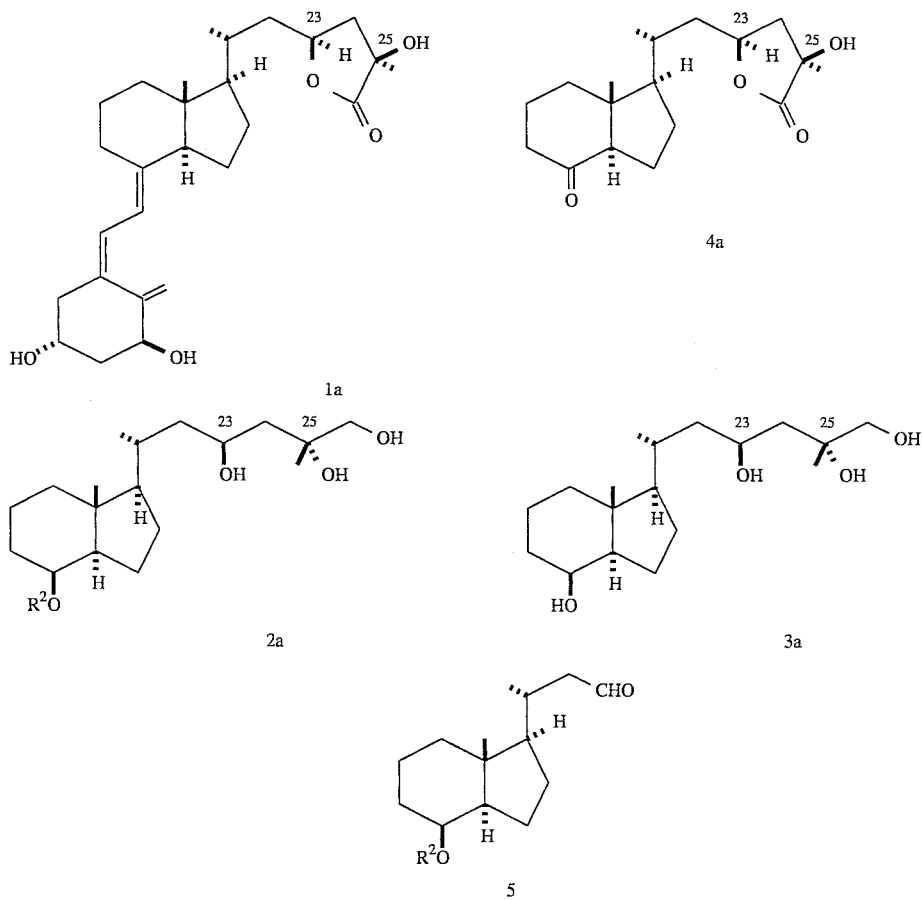

BACKGROUND OF THE INVENTION (23S, 25R)-Calcitriol lactone (1a) is a major mammalian metabolite of Vitamin D that has been shown to stimulate bone growth in osteoporotic rats (Seino, Y. et al., *Drugs of the Future* Vol. 17, p.655 (1992); see also, Japanese Kokai Patent Application No. 04095082A2 (1992)). Compound 1a is therefore useful for the study of, and potentially for the treatment of, osteoporosis and other diseases involving A bold line denotes a substituent projecting above the plane of the page; a dashed line denotes a substituent projecting below the plane of the page.

SUMMARY OF THE INVENTION

A much shorter and simpler process for transforming an aldehyde of formula 5 into tetrol 3a, and therefore into Compound 1a, has now been found. Commercially available enantiomerically pure (S)-2-methylglycidol (6S) is protected as a compound of formula 7S, which is in turn reductively cleaved with an aromatic radical anion. A hydrindane aldehyde compound of formula 5 is then added to the reaction mixture to form epimeric hydrindane diols. Then the protective group $R^1$ is removed from the hydrindane diols to yield an epimeric mixture of hydrindane triols 2a and 2b. These epimers can be separated before or after protective group $R^2$ is removed to produce hydrindane tetrols 3a and 3b. The hydrindane tetrol 3a ((8S,23S,25R)-De-A,B-cholestan- 8,23,25,26-tetrol) is then oxidized to yield Compound 4a. Finally, Compound 4a is transformed into Compound 1a by known methods. Likewise, hydrindane tetrol 3b can be oxidized to yield Compound 4b, and Compound 4b can be transformed into Compound 1b. Furthermore, Compounds 1c and 1d can be produced by the same process beginning with (R)-2-methylglycidol instead of (S)-2-methylglycidol. Hydrogen or lower-alkyl homologs of Compounds 1a, 1b, 1c, and 1d or their intermediates can also be prepared by analogous procedures beginning with enantiomerically pure glycidol or 2-alkylglycidol.

provide an improved process for synthesizing (23S,25R)-calcitriol lactone (Compound 1a).

Another object of the present invention is to provide an improved process for synthesizing the (23R,25R), (23R,25S), and (23S,25S) diastereoisomers (1b, 1c, and 1d respectively) of Compound 1a.

Another object of the present invention is to provide an efficient process for synthesizing multigram quantifies of Compounds 1a, 1b, 1c and 1d (collectively "Compounds 1").

Another object of the present invention is to provide an improved process for synthesizing certain diastereoisomers of compounds having the formula a, b, c or d:

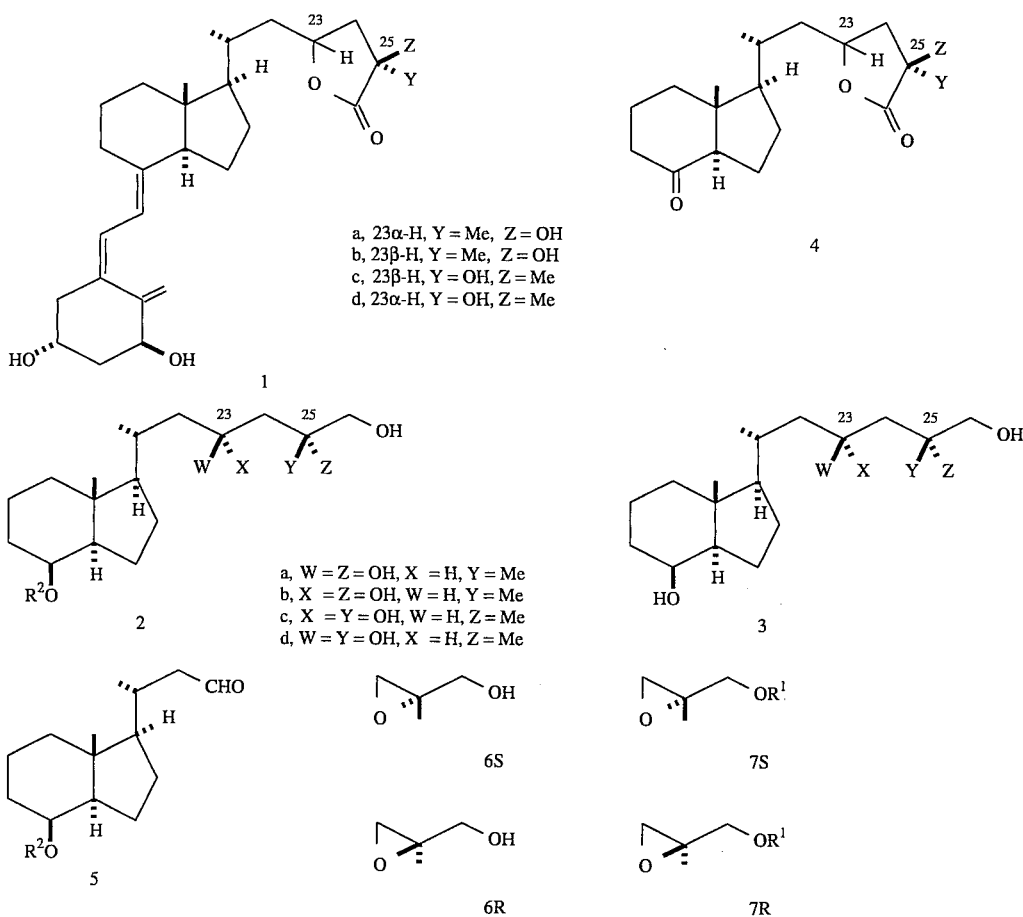

The descriptor β (beta) or a bold line denotes a substituent projecting above the plane of the page; the descriptor α (alpha) or a dashed line denotes a substituent projecting below the plane of the page.

Accordingly, an object of the present invention is to

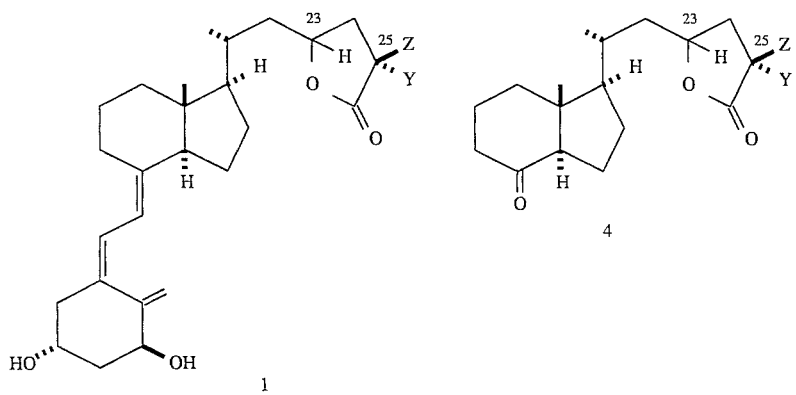

a, 23α-H; Y=H, $C_1$-$C_6$ alkyl, branched alkyl or cycloalkyl, saturated or unsaturated; Z=OH b, 23β-H; Y=H, $C_1$-$C_6$ alkyl, branched alkyl or cycloalkyl, saturated or unsaturated; Z=OH c, 23β-H; Y=OH; Z=H, $C_1$-$C_6$ alkyl, branched alkyl or cycloalkyl, saturated or unsaturated d, 23α-H; Y=OH; Z=H, $C_1$-$C_6$ alkyl, branched alkyl or cycloalkyl, saturated or unsaturated Another object of the present invention is to provide an improved process for synthesizing certain diastereoisomers of compounds having the formula a, b, c or d:

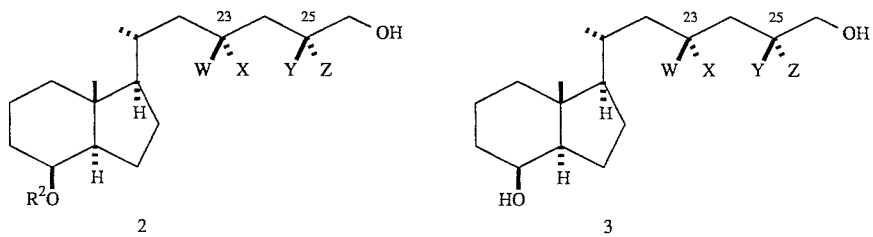

a, W=Z=OH; X=H; Y=H, $C_1$-$C_6$ alkyl, branched alkyl or cycloalkyl, saturated or unsaturated b, X=Z=OH; W=H; Y=H, $C_1$-$C_6$ alkyl, branched alkyl or cycloalkyl, saturated or unsaturated c, X=Y=OH; W=H; Z=H, $C_1$-$C_6$ alkyl, branched alkyl or cycloalkyl, saturated or unsaturated d, W=Y=OH; X=H; Z=H, $C_1$-$C_6$ alkyl, branched alkyl or cycloalkyl, saturated or unsaturated Still another object of the present invention is to provide an improved process for synthesizing related intermediates of Compounds 1 which are themselves biologically active as angiostatic agents.

These and other objectives and advantages of the present invention will become apparent from the following detailed description and examples.

DETAILED DESCRIPTION OF THE INVENTION

The process of the present invention is useful for synthesizing Compounds 1, homologs of Compounds 1, and their related intermediates. The synthesis of Compound 1a or 1b, or related intermediates, begins by obtaining enantiomerically pure (S)-2-methylglycidol (6S). The synthesis of Compound 1c or 1d, or related intermediates, begins by obtaining enantiomerically pure (R)-2-methylglycidol (6R). Compounds 6S and 6R are commercially available, for example from Aldrich Chemical Co., Milwaukee, Wis. The preparation of Compounds 2a and 2b beginning with enantiomerically pure (S)-2-methylglycidol (6S) is described below. To prepare Compounds 2c and 2d, an analogous procedure can be followed, beginning with enantiomerically pure (R)-2-methylglycidol (6R). The process of the present invention is also useful for synthesizing hydrogen or lower-alkyl homologs of Compound 1 or their intermedites. To prepare these homologs, analogous procedures can be followed, beginning with enantiomerically pure glycidol or 2-alkylglycidol.

The preparation of Compounds 2a and 2b begins by protecting the hydroxyl group of 6S with a suitable protective group $R^1$ to give a compound of formula 7S. Preferably, the protective group $R^1$ is (1-methyl-1-methoxy)ethyl so that Compound 6S is protected as its ((1-methyl-1-methoxy-)ethyl) ether (7S, R=$CMe_2OMe$). However, it is not essential that this protective group be chosen. Other protective groups and protection reactions are described in Greene et al., "Protective Groups in Organic Synthesis", 2nd ed., Wiley (1991), the entire contents of which are hereby incorporated by reference in the present specification.

The compound of formula 7S is then reductively cleaved by reaction with an aromatic radical anion. Preferably, the aromatic radical anion is lithium 4,4'-di-t-butylbiphenylide. The general procedure for this reductive cleavage reaction is known in the art and is described in Cohen et al., J. Org. Chem., Vol. 55, p. 1528 (1990), the entire contents of which are hereby incorporated by reference in the present invention. Then, a hydrindane aldehyde compound of formula 5 bearing a suitable hydroxyl protective group $R^2$ is added to the reductive cleavage reaction mixture to form hydrindane diols epimeric at carbon 23. The preferred protective group $R^2$ for the compound of formula 5 is a benzyl group. The preparation of Compound 5 ($R^2$=$CH_2Ph$) is taught in Johnson et al., at page 2599. However, it is not essential that $R^2$ be a benzyl group. Other protective groups and protection reactions are described in Greene et al.

$R^1$ is then removed from the hydrindane diols to yield an epimeric mixture of hydrindane triols 2a and 2b. In the preferred case where $R^1$ is (1-methyl-1-methoxy)ethyl, the protective group is removed by reaction with dilute aqueous acid, preferably sulfuric acid.

Preferably, 2a and 2b are separated prior to removal of $R^2$. In this case, the separation is preferably achieved by chromatography on silica gel, but can also be accomplished by other known methods.

$R^2$ is removed from the hydrindane triol 2a or 2b to produce hydrindane tetrol 3a or 3b, respectively. Alternatively, $R^2$ is removed from the epimeric mixture of 2a and 2b to produce the hydrindane tetrol mixture of 3a and 3b. This triol to tetrol conversion is effected by known methods, such as those described in the above-cited publication of Greene et at. In the preferred case where $R^2$ is a benzyl group, the hydrindane triol to tetrol conversion can be effected by catalytic hydrogenolysis. This procedure is described by Greene et at. at page 47.

At least one diastereoisomer of formula 3, namely Compound 3a, has been shown to be biologically active as a potent angiostatic agent. Commonly assigned U.S. patent application Ser. No. 07/930,635, filed Aug. 17, 1992, the entire contents of which are hereby incorporated by reference in the present specification, teaches that substituted hydrindanes, such as those having the structure of Compound 3a, are useful in treating neovascularization associated with, for example: cancer, solid tumors, arthritis, diabetes, arteriosclerosis, angiofibroma, arteriovenous malformatios, corneal graft neovascularization, delayed wound healing, diabetic retinopathy, age related macular degeneration, granulations, burns, hemangioma, hemophilic joints, hypertrophic scars, neovascular glaucoma, nonunion fractures, Osier-Weber Syndrome, psoriasis, pyogenic granuloma, retrolental fibroplasia, pterigium, scleroderma, trachoma, vascular adhesions, ocular neovascularization, parasitic diseases, hypertrophy following surgery, inhibition of hair growth, inhibition of ovulation and corpus luteum formation and inhibition of embryo implantation and development in the uterus.

In order to produce the vitamin D metabolite 1a from Compound 3a, known procedures are employed. Keto lactone 4a is obtained by oxidizing the hydrindane tetrol 3a. The oxidation of Compound 3a can be accomplished by known reactions, such as the procedure described by Johnson et al., at page 2600.

The Lythgoe-type coupling of keto lactone 4a to give Compound 1a is also accomplished by known procedures, such as the procedure disclosed by Wovkulich et al. This procedure entails protection of the hydroxyl group of 4a, preferably as a trimethylsilyl ether; reaction of protected 4a with the lithium salt of (3S)-(3α,5β,Z)-2-(2-methylene- 3,5-bis-((1,1-dimethylethyl)dimethylsilyloxy)cyclohexylidine)ethyl diphenyl phosphine oxide; and finally removal of the hydroxyl protective groups from the product, for example by reaction of the product with methanol in the presence of a cation exchange resin.

In a like manner, Compounds 1b, 1c or 1d can be made beginning with Compounds 3b, 3c or 3d, respectively.

The process of the present invention is especially convenient because of the commercial availability of enantiomerically pure 6S and 6R. By choosing the appropriate enantiomer, a desired diastereoisomer of Compound 3, 4, or 1 can be produced since the present process controls the stereochemistry at the critical chiral centers (carbons 23 and 25) of these compounds.

As will be apparent to one skilled in the art, the process of the present invention is also useful for producing homologs of Compounds 1 or their intermediates. In particular, homologs which contain either hydrogen or lower alkyl groups (about 6 carbon atoms or less, saturated or unsaturated, in place of the methyl group on carbon 25) can be prepared from the corresponding homologs of 6S or 6R. Homologs which contain hydrogen can be prepared using an analogous process beginning with commercially available enantiomerically pure glycidol. Similarily, homologs which contain lower alkyl, branched alkyl or cycloalkyl groups, saturated or unsaturated, can be prepared using an analogous process beginning with a saturated or unsaturated lower alkyl-, branched alkyl- or cycloalkylglycidol. Suitable enantiomerically pure 2-alkylglycidols may be prepared by methods known in the art, such as are taught in European Patent Application Publication No. 0454463 A2 (Oct. 30, 1991).

The following examples are offered to specifically illustrate this invention. These examples and illustrations are not to be construed in any way as limiting the scope of this invention.

EXAMPLE 1

Preparation of (R)-2-((1-methyl-1-methoxy)ethoxy)methyl-2-methyloxirane (7S, $R^1$=$CMe_2OMe$)

Pyridinium p-toluenesulfonate (0.15 g, 0.60 mmol) was added to a stirred solution of 2-methoxypropene (8.0 mL, 83 mmol) and 6S (Aldrich, 4.98 g, 56.6 mmol) in 20 mL of dry dichloromethane under argon. A vigorous reflux ensued. Filtration through Florisil (eluting with diethyl ether), concentration and purification by chromatography on silica (1:1 diethyl ether-hexane) afforded 7.29 g (80%) of 7S ($R^1$=$CMe_2OMe$) as a volatile oil, $[\alpha]_D^{23}$+4.7° (c=1.4, methanol). IR (film) 2990, 1461, 1376, 1256, 1213(sh 1190), 1050(sh 1075), 902, 858, 817 $cm^{-1}$. NMR($CDCl_3$): δ 1.35 (s, 6H); 1.39 (s, 3H); 2.71 (AB, 2H); 3.21 (s, 3H); 3.43 (AB, 2H). Anal. calcd: C, 59.97; H, 10.07. Found: C, 60.05; H, 9.99.

EXAMPLE 2

Preparation of (8S,23S,25R)-De-A,B-8-(benzyloxy)cholestan-23,25,26-triol (2a,$R_2$=$CH_2Ph$)

A stirred, ice-cooled solution of 4,4'-di-t-butylbiphenyl (8.5 g, 32 mmol) and 5 mg of 2,2'-bipyridyl in 90 mL of tetrahydrofuran (distilled from potassium/benzophenone) under argon was titrated to dryness with n-butyllithium (red endpoint). Lithium wire (1% sodium, 0.21 g, 30 mmol, 0.3 cm pieces) was added, the mixture was stirred for 5.5 hours, then cooled to −70° C. (internal). Epoxy ether 7S ($R^1$=$CMe_2OMe$) (2.54 g, 16 mmol) was added (<−65° C.), followed after 6 minutes by a solution of 5 (2.43 g, 7.74 mmol) in 10 mL of anhydrous tetrahydrofuran. The mixture was stirred for 4 hours (to 8° C.), quenched with saturated aqueous potassium dihydrogen phosphate, and the phases were separated. The separated organic solution was stirred with 0.25M aqueous sulfuric acid for 18 hours. The product was isolated by extraction (ethyl acetate-water) and purified by chromatography on silica (55% ethyl acetate-hexane-ethyl acetate) yielding 1.03 g (33%) of 2b ($R^2$=CH2Ph), followed by 1.12 g (36%) of 2a ($R^2$=CH$_2$Ph). NMR (CDCl$_3$) of 2b: δ0.97 (d, 3H); 0.99 (s, 3H); 1.24 (s, 3H); 1.0–2.1 (m, 18H); 2.7 (br s, 2H); 3.42 (s, 2H); 3.70 (s, 1H); 4.18 (t, 1H); 4.48 (AB, 2H); 7.3 (m, 5H). NMR (CDCl$_3$) of 2a; δ0.93 (d, 3H); 0.96 (s, 3H); 1.22 (s, 3H); 1.0–2.1 (m, 18H); 2.8 (br s, 2H); 3.58 (AB, 2H); 3.70 (s, 1H); 4.02 (t, 1H); 4.48 (AB, 2H); 7.3 (m, 5H).

EXAMPLE 3

Preparation of
(8S,23S,25R)-De-A,B-cholestan-8,23,25,26-tetrol
(3a)

A solution of 2a ($R^2$=CH$_2$Ph) (0.71 g) in 40 mL of methanol containing 0.40 g of 10% palladium on charcoal was hydrogenated (3 atmospheres hydrogen pressure, 24h). Filtration through Celite and concentration gave 0.55 g (99%) of 3a. Recrystallization (n-chlorobutane-methanol) gave the analytical sample of 3a (0.26 g), $[\alpha]_D^{23}$+67.1° (c=1, methanol), colorless prisms, m.p. 181°–183.5° C., literature m.p. 178°–180° C. IR (KBr) 3278 (vs), 2932, 1442(sh 1480), 1052, 731 cm$^{-1}$. NMR (DMSO-d$_6$): δ 0.86 (d, 3H); 0.86 (s, 3H); 1.05 (s, 3H); 0.9–2.0 (m, 17H); 3.2 (ABX, 2H); 3.77 (s, 1H); 3.85 (s, 1H); 415 (d, 1H, x); 4.56 (s, 1H, x); 4.6–4.7 (m, 2H, x); x=exchanges with D$_2$O. Anal. calcd: C, 68.75; H, 10.90. Found: C, 68.85; H, 10.91.

I claim:

1. A process for synthesizing diastereoisomers a, b, c or d of a compound of the formula

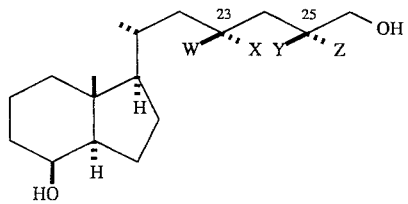

wherein in diastereoisomer a, X=H; W=Z=OH; and Y=H, $C_1$–$C_6$ alkyl, branched alkyl or cycloalkyl, saturated or unsaturated;

in diastereoisomer b, X=Z=OH; W=H; and Y=H, $C_1$–$C_6$ alkyl, branched alkyl or cycloalkyl, saturated or unsaturated;

in diastereoisomer c, X=Y=OH; W=H; and Z=H, $C_1$–$C_6$ alkyl, branched alkyl or cycloalkyl, saturated or unsaturated;

in diastereoisomer d, W=Y=OH; X=H; and Z=H, $C_1$–$C_6$ alkyl, branched alkyl or cycloalkyl, saturated or unsaturated;

which comprises the steps of:
(a) protecting the hydroxyl group of enantiomerically pure glycidol or 2-alkylglycidol with a suitable first protective group;
(b) reductively cleaving the protected product of step (a) with an aromatic radical anion;
(c) reacting the cleaved product of step (b) with De-A, B-8β-hydroxy-24-nor-cholan- 23-al which has had its hydroxyl group protected with a suitable second protective group to form epimeric hydrindane diols;
(d) removing the first protective group from the hydrindane diol product of step (c) to yield an epimeric mixture of hydrindane triols;
(e) separating the epimeric hydrindane triol isomers of step (d); and
(f) removing the second protective group from the separated epimeric hydrindane triol isomers of step (e) to yield hydrindane tetrols.

2. The process of claim 1 wherein in diastereoisomers a and b, Y=Me, and in diastereoisomers c and d, Z=Me; and the glycidol compound in step (a) is 2-methylglycidol.

3. The process of claim 2 wherein the aromatic radical anion is lithium 4,4'-di-t-butylbiphenylide.

4. The process of claim 2 wherein the separation in step (e) is accomplished by chromatography on silica.

5. The process of claim 2 wherein the first protective group is a (1-methyl-1-methoxy)ethyl group and the second protective group is a benzyl group.

6. The process of claim 5 wherein the first protective group is removed in step (d) by mixing the product of step (c) with a dilute aqueous acid.

7. The process of claim 6 wherein the dilute aqueous acid is sulfuric acid.

8. The process of claim 5 wherein the second protective group is removed in step (f) by catalytic hydrogenolysis.

9. The process of claim 2 wherein the first protective group is a (1-methyl-1methoxy)ethyl group; the second protective group is a benzyl group; the aromatic radical anion is lithium 4,4'-di-t-butylbiphenylide; the first protective group is removed in step (d) by mixing the product of step (c) with dilute sulfuric acid; the separation in step (e) is accomplished by chromatography on silica; and the second protective group is removed in step (f) by catalytic hydrogenolysis.

10. A process for synthesizing diastereoisomers a, b, c or d of a compound of the formula

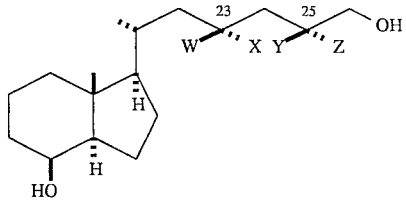

wherein in diastereoisomer a, X=H; W=Z=OH; and Y=H, $C_1$–$C_6$ alkyl, branched alkyl or cycloalkyl, saturated or unsaturated;

in diastereoisomer b, X=Z=OH; W=H; and Y=H, $C_1$–$C_6$ alkyl, branched alkyl or cycloalkyl, saturated or unsaturated;

in diastereoisomer c, X=Y=OH; W=H; and Z=H, $C_1$–$C_6$ alkyl, branched alkyl or cycloalkyl, saturated or unsaturated;

in diastereoisomer d, W=Y=OH; X=H; and Z=H, $C_1$–$C_6$ alkyl, branched alkyl or cycloalkyl, saturated or unsaturated;

which comprises the steps of:
(a) protecting the hydroxyl group of enantiomerically pure glycidol or 2-alkylglycidol with a suitable first protective group;
(b) reductively cleaving the protected product of step (a) with an aromatic radical anion;
(c) reacting the cleaved product of step (b) with De-A, B-8β-hydroxy-24-nor-cholan-23-al which has had its hydroxyl group protected with a suitable second protective group to form epimeric hydrindane diols;

(d) removing the first protective group from the hydrindane diol product of step (c) to yield an epimeric mixture of hydrindane triols;

(e) removing the second protective group from the epimeric hydrindane triol isomers of step (d) to yield hydrindane tetrols; and (f) separating the epimeric hydrindane tetrol isomers.

11. The process of claim 10 wherein in diastereoisomers a and b, Y=Me, and in diastereoisomers c and d, Z=Me; and the glycidol compound in step (a) is 2-methylglycidol.

12. The process of claim 11 wherein the aromatic radical anion is lithium 4,4'-di-t-butylbiphenylide.

13. The process of claim 11 wherein the first protective group is a (1-methyl-1methoxy)ethyl group and the second protective group is a benzyl group.

14. The process of claim 13 wherein the first protective group is removed in step (d) by mixing the product of step (c) with a dilute aqueous acid.

15. The process of claim 14 wherein the dilute aqueous acid is sulfuric acid.

16. The process of claim 13 wherein the second protective group is removed in step (e) by catalytic hydrogenolysis.

17. The process of claim 11 wherein the first protective group is a (1-methyl-1methoxy)ethyl group; the second protective group is a benzyl group; the aromatic radical anion is lithium 4,4'-di-t-butylbiphenylide; the first protective group is removed in step (d) by mixing the product of step (c) with dilute aqueous acid; and the second protective group is removed in step (e) by catalytic hydrogenolysis.

* * * * *